(12) United States Patent
Handel et al.

(10) Patent No.: US 8,518,005 B2
(45) Date of Patent: Aug. 27, 2013

(54) SEALING PATTERN FOR TAMPON OVERWRAP

(71) Applicants: McNeil-PPC, Inc., Skillman, NJ (US); Johnson & Johnson GmbH, Neuss (DE)

(72) Inventors: Otto Handel, Constance (DE); Stephan M. Linkel, Ewing, NJ (US); Simone Weitz, Köln (DE)

(73) Assignees: McNeil-PPC, Inc., Skillman, NJ (US); Johnson & Johnson GmbH, Neuss, DE (US)

( * ) Notice: Subject to any disclaimer, the term of this patent is extended or adjusted under 35 U.S.C. 154(b) by 0 days.

(21) Appl. No.: 13/717,893

(22) Filed: Dec. 18, 2012

(65) Prior Publication Data
US 2013/0110069 A1    May 2, 2013

Related U.S. Application Data

(62) Division of application No. 12/621,764, filed on Nov. 19, 2009, now Pat. No. 8,357,134.

(60) Provisional application No. 61/118,118, filed on Nov. 26, 2008.

(51) Int. Cl.
*A61F 13/20*    (2006.01)

(52) U.S. Cl.
USPC ............... 604/385.02; 604/385.17; 604/904

(58) Field of Classification Search
USPC ............... 604/385.02, 385.17, 385.18, 904; 206/438, 440, 495; 229/87.01, 87.05; 383/206, 383/207
See application file for complete search history.

(56) References Cited

U.S. PATENT DOCUMENTS

| 1,560,681 | A | * | 11/1925 | Fisher | ............... 206/384 |
| 3,092,251 | A | | 6/1963 | Jaggers | |

(Continued)

FOREIGN PATENT DOCUMENTS

| EP | 213241 A | 3/1987 |
| EP | 226834 A | 7/1987 |

(Continued)

OTHER PUBLICATIONS

In the USPTO U.S. Appl. No. 12/621,744 the Restriction Requirement dated Aug. 10, 2012.

(Continued)

*Primary Examiner* — Jackie Ho
*Assistant Examiner* — Kathryn E Ditmer

(57) ABSTRACT

Tampons are packaged in a substantially cylindrical wrapper formed of a flexible, sheet-like material that is closed with one or more attachment zones having one or more gaps crossed by a line of weakness. The wrapper is closed at both ends and has a longitudinal seam area in which overlapping portions of the flexible, sheet-like material are attached. The longitudinal seam area comprises a substantially longitudinal attachment zone with a first edge and a second edge that defines a seam area. The line of weakness has a first end disposed within the seam area at a distance from a first end of the wrapper package; extends through a gap in the substantially longitudinal attachment zone; continues generally circumferentially about the wrapper; and terminates at a second end disposed within the seam area at the second edge of the substantially longitudinal attachment zone. The line of weakness extends across the seam area, and the wrapper can be removed as a single piece.

8 Claims, 14 Drawing Sheets

(56) References Cited

U.S. PATENT DOCUMENTS

| | | | |
|---|---|---|---|
| 3,135,262 | A | 6/1964 | Kobler et al. |
| 3,278,013 | A | 10/1966 | Banks |
| 3,309,006 | A | 3/1967 | Perry et al. |
| 3,766,703 | A | 10/1973 | Simon et al. |
| 3,777,632 | A | 12/1973 | Pepmeier |
| 3,814,099 | A | 6/1974 | Kobler |
| 3,856,143 | A | 12/1974 | Simon et al. |
| 4,053,046 | A | 10/1977 | Roark |
| 4,170,305 | A | 10/1979 | Hull, Jr. et al. |
| 4,557,385 | A | 12/1985 | Robinson |
| 4,610,659 | A | 9/1986 | Friese |
| 4,617,781 | A | 10/1986 | Ingersoll et al. |
| 4,648,513 | A | 3/1987 | Newman |
| 4,765,477 | A | 8/1988 | Froidh et al. |
| 4,816,100 | A | 3/1989 | Friese |
| 4,881,644 | A | 11/1989 | Norquest et al. |
| 5,054,264 | A | 10/1991 | Miller |
| 5,133,457 | A | 7/1992 | Kadel |
| 5,180,059 | A | 1/1993 | Shimatani et al. |
| 5,365,719 | A | 11/1994 | Council |
| 5,409,115 | A | 4/1995 | Barkhorn |
| 5,462,166 | A | 10/1995 | Minton et al. |
| 5,478,336 | A | 12/1995 | Pigneul |
| 5,792,131 | A | 8/1998 | Mizutani |
| 5,911,712 | A | 6/1999 | Leutwyler et al. |
| 6,036,679 | A | 3/2000 | Balzar et al. |
| 6,041,928 | A | 3/2000 | Jousinen et al. |
| 6,053,318 | A | 4/2000 | Petterson |
| 6,063,065 | A | 5/2000 | Costa |
| 6,115,997 | A | 9/2000 | Burrow |
| 6,183,457 | B1 | 2/2001 | Kuhn |
| 6,250,468 | B1 | 6/2001 | Huchel |
| 6,299,607 | B1 | 10/2001 | Osborn, III et al. |
| 6,310,296 | B1 | 10/2001 | Nishi et al. |
| 6,352,364 | B1 | 3/2002 | Möbs |
| 6,446,795 | B1 | 9/2002 | Allen et al. |
| 6,478,763 | B1 | 11/2002 | Simonsen et al. |
| 6,955,665 | B2 | 10/2005 | Domeier et al. |
| 6,994,696 | B2 | 2/2006 | Suga |
| 7,065,939 | B2 | 6/2006 | Wasson et al. |
| 7,073,666 | B2 | 7/2006 | Arndt |
| 7,101,358 | B2 | 9/2006 | Domeier et al. |
| 7,413,079 | B2 | 8/2008 | Hermansson et al. |
| 7,422,105 | B2 | 9/2008 | Loyd et al. |
| 2003/0065300 | A1 | 4/2003 | Suga |
| 2003/0220624 | A1 | 11/2003 | Domeier et al. |
| 2003/0220625 | A1 | 11/2003 | Domeier et al. |
| 2003/0233813 | A1 | 12/2003 | Leslie et al. |
| 2004/0133142 | A1 | 7/2004 | Lochte et al. |
| 2007/0156109 | A1 | 7/2007 | Loyd et al. |
| 2008/0058749 | A1 | 3/2008 | Tackett et al. |
| 2008/0064581 | A1 | 3/2008 | Lochte et al. |
| 2008/0105579 | A1 | 5/2008 | Arndt |
| 2008/0118679 | A1 | 5/2008 | McConnell et al. |
| 2009/0069769 | A1 | 3/2009 | Minoguchi et al. |
| 2009/0188825 | A1 | 7/2009 | McConnell |
| 2010/0130953 | A1 | 5/2010 | Fung et al. |
| 2010/0130954 | A1 | 5/2010 | Handel et al. |

FOREIGN PATENT DOCUMENTS

| | | |
|---|---|---|
| EP | 597446 A | 5/1994 |
| EP | 807075 A | 11/1997 |
| EP | 1618860 A | 1/2006 |
| WO | WO 02/067837 A | 9/2002 |
| WO | WO 03/082174 A | 10/2003 |
| WO | WO 2004/080362 A | 9/2004 |
| WO | WO 2008/046036 A | 4/2008 |

OTHER PUBLICATIONS

In the USPTO U.S. Appl. No. 12/621,744 the Non-final Rejection dated Oct. 26, 2012.

In the USPTO U.S. Appl. No. 12/621,764, the Restriction Requirement dated Aug. 10, 2012.

In the USPTO U.S. Appl. No. 12/621,764, the Notice of Allowance dated Oct. 29, 2012.

In the USPTO U.S. Appl. No. 13/750,396 the Non-final rejection dated Mar. 29, 2013.

\* cited by examiner

SEALING PATTERN FOR TAMPON OVERWRAP

This application is a divisional application of U.S. application Ser. No. 12/621,764 filed Nov. 19, 2009, which claims the benefit of U.S. provisional application 61/118,118 filed on Nov. 26, 2008, the complete disclosures of which are hereby incorporated herein by reference for all purposes.

FIELD OF THE INVENTION

The present invention relates to a wrapper for an individual absorbent article such as a tampon. In particular, the invention relates to the sealing of a tampon wrapper such that the formed seal does not impede the opening mechanism, which extends around the perimeter of the absorbent article.

BACKGROUND OF THE INVENTION

Individual absorbent articles for personal hygiene articles are protected from the environment by sheets of material commonly referred to as wrappers or overwrap. Tampons, in particular, have employed wrappers in which each tampon is encased in a separate primary package, which may be then be sold in quantity in secondary packaging, often a box.

Tampons are generally categorized in two classes: applicator tampons and digital tampons. The wrapper for an applicator tampon is typically elongated, loose fitting, and flange or fin sealed at the ends with a small cut or notch at one end which the user uses to tear open the wrapper in a longitudinal fashion. The wrapper for a digital tampon is typically tight fitting, often contacting the outer surface of the tampon completely about the perimeter. Typically, the wrapper for a digital tampon resembles a tube where two longitudinal margins overlap. The wrapper is sealed at both the insertion and withdrawal end. The longitudinal overlap is also sealed, usually by heat. This tight wrapping may help maintain the shape of the tampon and prevent deformation.

Examples of wrapper sealing for both digital tampons and applicator tampons may be found on in U.S. Pat. No. 4,170, 305 (Hull et al.); WO 03/082174 (Schoelling et al.); U.S. Pat. No. 6,955,665 (Domeier et al.); U.S. Pat. No. 7,101,358 (Domeier et al.); and U.S. 2008/0118679 (McConnell et al.).

U.S. Pat. No. 4,170,305 discloses a wrapper for a cylindrical body which is tightly wrapped, clean, dust proof and easily opened. The wrapper has two perforations zones, and double wrapping such that the zones are off set so as to close any pathway into the product. The ends of the wrapper are sealed by means such as heat sealing. The tampon is unwrapped by simply lifting and gripping a tab, resulting in the two layers coming off together, separating the wrapper into multiple pieces. The wrapper extends at least twice the radial circumference of the tampon body.

WO 03/082174 discloses a packaging material having at least one line of weakness. After destruction of the line, the wrapper can be peeled off the product, preferably in one piece. The end points of the packaging material sheet can be reinforced in order to prevent the packaging material from tearing beyond the end points.

U.S. Pat. No. 6,955,665 purports to disclose wrapper for an individually packaged tampon. The wrapper has an opening means made of at least one line of weakness, which does not extend around the whole wrapped tampon in terms of length or perimeter. Because of this, the wrapper is prevented from becoming separated into several pieces of wrapper material upon opening of the wrapper, which is facilitated by tearing along the line of weakness.

U.S. Pat. No. 7,101,358 purports to disclose a wrapper for individually wrapped tampons, which includes a line of weakness having an opening means which includes a stopper. The opening means is a tear tape and the stopper prevents the separation of the tear tape from at least one segment of the wrapper material, which is generated upon opening of the wrapper. As the wrapper is formed by closing the wrapper material onto itself a seam is generated in the regions of the wrapper. The tear tape can extend around the whole tampon lengthwise or around the whole perimeter of the tampon or both. The stopper may be substantially coextensive with at least part of the seam.

U.S. 2008/0118679 purports to disclose a wrapper that provides predictable and easy opening, discrete disposal and the ability to remain in one piece after opening. The wrapper includes one or more lines of weakness, which can be disposed at an angle with respect to a longitudinal axis of the wrapper. The line of weakness can extend around less than about 95% of the periphery and may have an initiation point. The wrapper may have a back or side seal.

In this invention, even though the line of weakness extends completely around the wrapped tampon, the overwrap remains in one piece when opened. This overcomes some of the disadvantages of the above prior art such as providing the user with a hygienic wrapped tampon, an easy way to remove the tampon from the overwrap, a single piece of waste to dispose of and less manipulation of the overwrap. This is accomplished by sealing the edges of a tampon wrapper such that the perforations forming the opening mechanism are not impeded or compromised. This allows the overwrap to be easily opened in order to remove the enclosed tampon without the overwrap separating into multiple pieces of material.

SUMMARY OF THE INVENTION

We have found a packaged elongate intravaginal device that allows for removal of the device from the wrapper while keeping the wrapper as a unitary piece of material.

Tampons are packaged in a substantially cylindrical wrapper formed of a flexible, sheet-like material that is closed with one or more attachment zones having one or more gaps crossed by a line of weakness.

In one embodiment of the invention, a tampon is packaged in a substantially cylindrical wrapper formed of a flexible, sheet-like material that is closed with a single attachment zone having one gap with a line of weakness extending through the gap. The wrapper is closed at both ends and has a longitudinal seam area in which overlapping portions of the flexible, sheet-like material are attached. The longitudinal seam area comprises a substantially longitudinal attachment zone with a first edge and a second edge that defines a seam area. The line of weakness has a first end disposed within the seam area at the first edge of the substantially longitudinal attachment zone at a distance from a first end of the wrapper package; extends through a gap in the substantially longitudinal attachment zone and to the second edge of the substantially longitudinal attachment zone; continues generally circumferentially about the wrapper; extends through the gap in the substantially longitudinal attachment zone, and terminates at a second end disposed within the seam area at the second edge of the substantially longitudinal attachment zone.

In another embodiment of the invention, a tampon is packaged in a substantially cylindrical wrapper formed of a flexible, sheet-like material that is closed with two attachment zones—each having a gap—and a line of weakness extends through the gaps. The wrapper is closed at both ends and has a longitudinal seam area in which overlapping portions of the flexible, sheet-like material are attached. The longitudinal seam area comprises a first, substantially longitudinal attachment zone that defines a first side of the seam area and a second substantially longitudinal attachment zone, opposite the first substantially longitudinal attachment zone that defines a second side of the seam area. The line of weakness has a first end disposed within the seam area at a first distance from a first end of the wrapper package and adjacent the first substantially longitudinal attachment zone; extends through a gap in the second substantially longitudinal attachment zone; continues generally circumferentially about the wrapper; extends through a gap in the first substantially longitudinal attachment zone at a second distance from the first end of the wrapper/package, and terminates at a second end disposed within the seam area adjacent the second substantially longitudinal attachment zone.

In another embodiment of the invention, a tampon is packaged in a substantially cylindrical wrapper formed of a flexible, sheet-like material that is closed with three attachment zones—each having at least one gap—and a line of weakness extends through the gaps. The wrapper is closed at both ends and has a longitudinal seam area in which overlapping portions of the flexible, sheet-like material are attached. The longitudinal seam area comprises a first, substantially longitudinal attachment zone that defines a first side of the seam area and a second substantially longitudinal attachment zone, opposite the first substantially longitudinal attachment zone that defines a second side of the seam area, and a third substantially longitudinal attachment zone located between the first and the second substantially longitudinal attachment zones. The line of weakness has a first end disposed within the seam area at a first distance from a first end of the wrapper package and adjacent the second substantially longitudinal attachment zone; extends through gaps in the first and third substantially longitudinal attachment zones; continues generally circumferentially about the wrapper; extends through gaps in the second and third substantially longitudinal attachment zones at a second distance from the first end of the wrapper/package, and terminates at a second end disposed within the seam area adjacent the first substantially longitudinal attachment zone.

In another embodiment of the invention, a method of packaging a tampon includes the steps of providing a wrapper blank comprising a flexible, sheet-like material having a length and a width and at least one line of weakness extending across substantially all of the width; forming the wrapper blank into a wrapper tube having first and second ends, a length corresponding to the length of the wrapper blank, and an overlapping longitudinal seam area having two plies of the flexible, sheet-like material; forming a longitudinal seam within the seam area by attaching portions of the two plies together in a pattern; closing the first end of the tube; inserting the tampon into the tube; and closing the second end of the tube. The wrapper tube has a first, substantially longitudinal attachment zone that defines a first side of the seam area and a second substantially longitudinal attachment zone, opposite the first substantially longitudinal attachment zone that defines a second side of the seam area. The second substantially longitudinal attachment zone has a gap formed therein proximate a first end thereof corresponding to the first end of the wrapper tube, and the first substantially longitudinal attachment zone has a gap formed therein proximate a first end thereof corresponding to the first end of the wrapper tube. The gap in the second substantially longitudinal attachment zone is nearer the first end of the wrapper tube than the gap in the first substantially longitudinal attachment zone. The line of weakness has a first end disposed within the seam area adjacent the first substantially longitudinal attachment zone, extends through the gaps in the second and first substantially longitudinal attachment zones, and has a second end disposed within the seam area adjacent the second substantially longitudinal attachment zone.

DETAILED DESCRIPTION OF THE PREFERRED EMBODIMENTS

Absorbent tampons usually incorporate elongate compressed absorbent structures, such as substantially cylindrical masses of compressed absorbent material having a central longitudinal axis and a radius that defines the outer circumferential surface of the tampon. Tampons are often formed by first obtaining a shaped mass of absorbent material called a tampon blank. This blank can be in the form of a roll of sheet-like material, a segment of a continuous absorbent material, a mass of randomly or substantially uniformly oriented absorbent material, an individually prepared or cast mass of absorbent material, and the like.

The tampon blank is relatively uncompressed and has a relatively low density. It is then compressed to form a product having overall dimensions less than those of the blank prior to use. The compressed tampons may have a generally uniform density throughout the tampon or they may have regions of differing density as described in the commonly assigned applications to Friese et al., U.S. Pat. No. 6,310,296, and Leutwyler et al., U.S. Pat. No. 5,911,712, the disclosures of which are herein incorporated by reference. Tampons also usually include a cover or some other surface treatment and a withdrawal string or other removal mechanism.

By 'outer surface' of the tampon, it is meant herein the visible surface of the compressed tampon prior to use or expansion.

By 'length' of a tampon, it is meant herein the linear extension of a tampon along its largest dimension.

By 'perimeter' of a tampon, it is meant herein the distance measured along the outer surface of the tampon in a portion of said outer surface extending in a plane being substantially perpendicular to the dimension of the length of said tampon. In other words, the length of the tampon extends along the x-axis of an orthogonal Cartesian coordinate system and the perimeter typically lies in the y,z-plane of said coordinate system.

As used herein, the terms "weakness component" and "line of weakness" shall mean a series of weakness points arranged in a row. These weakness points may be perforations, areas of reduced thickness, slits, score lines, areas of reduced density, etc.

The term "overwrap" as used herein refers to a structure, which is formed of a sheet of material and which substantially encloses an individual intravaginal device. The term "intravaginal device" may mean those devices designed to be placed within the vaginal canal such a tampon, or incontinent/pessary device. The overwrap has two ends, each of them being assigned to an end of the wrapped tampon. Typically, suitable wrapper materials for use herein are flexible polymeric films. The film used may have any thickness.

Figure 1:
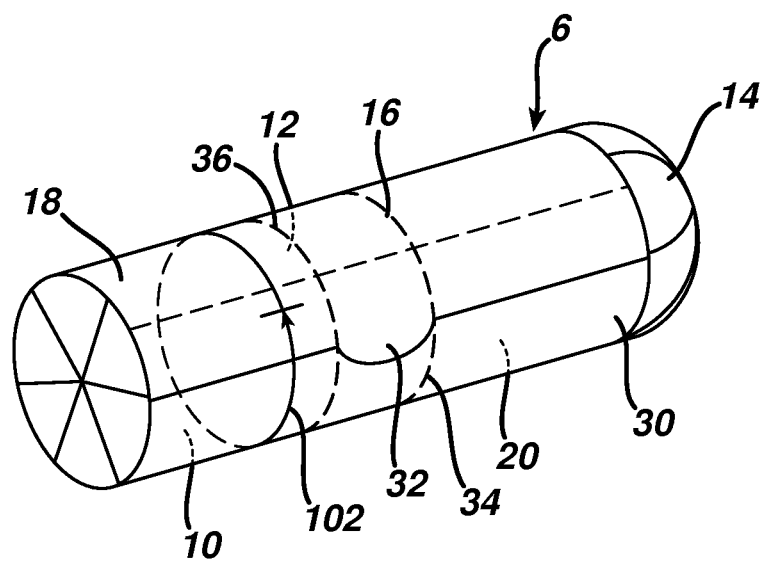
FIG. 1 is a perspective view of an example of a packaged tampon of the prior art.

An example of a packaged tampon 6 known in the prior art is illustrated in FIG. 1. The packaged tampon 6 contains tampon 10 within an overwrap 30. Tampon 10 has a compressed, elongate absorbent structure 12 having a length, an insertion end 14, a withdrawal end 18 and a central portion 16 located between the insertion end and withdrawal end. The withdrawal end may include a string (not shown). Tampon 10 has an outer surface 20 and perimeter 102, which extends 360° around the tampon.

In the example shown in FIG. 1, the overwrap 30 has an opening mechanism. In this example of prior art, the overwrap has a finger lift tab 32, which allows the user to tear open the overwrap along perforated lines 34 and 36 that extend around the overwrap. Typically, this type of opening mechanism results in the overwrap being torn into multiple portions—a central portion having a width which corresponds to the finger lift dimension, a portion covering the insertion end and a portion covering the withdrawal end. Once the user has opened the overwrap by lifting and separating the finger lift tab, the user may additionally have to peel off the remaining portions. This remains an inconvenience for the user as she now has to use both hands to unwrap the tampons while dealing with the multiple pieces, which may have static charges causing the pieces to cling to her hands, her fingers, and/or the tampon. This can increase the risk of the overwrap remaining on the tampon when it is inserted into the user's body. This remaining piece of overwrap may disengage from the tampon as the tampon absorbs fluid, thereby remaining in the body until removed by the user.

This uncontrolled opening of the wrapper may also occur in thinner packaging materials in which the tear may not follow a predetermined path along a line of weakness and may also result in multiple pieces of the destroyed wrapper.

The wrappers can generally be formed of a sheet or one connected piece of overwrap material, though an overwrap can be made from multiple pieces of material sufficiently joined together such that they substantially act as a single sheet or one connected piece of overwrap material. In FIG. 1, the material is joined together by any means known in the art. Where the material is joined is commonly referred to as a seam. The overwrap may be clear, colored, or have printed graphics, which may include directions for opening (arrows, dotted lines, etc.).

Figure 2:
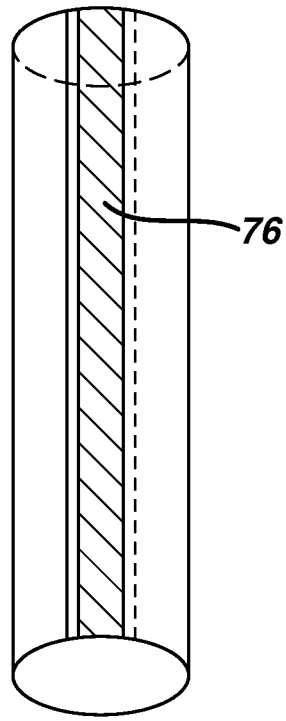
FIG. 2 is a perspective view of a tube used to form an overwrap for a tampon of the prior art.
Figure 3:
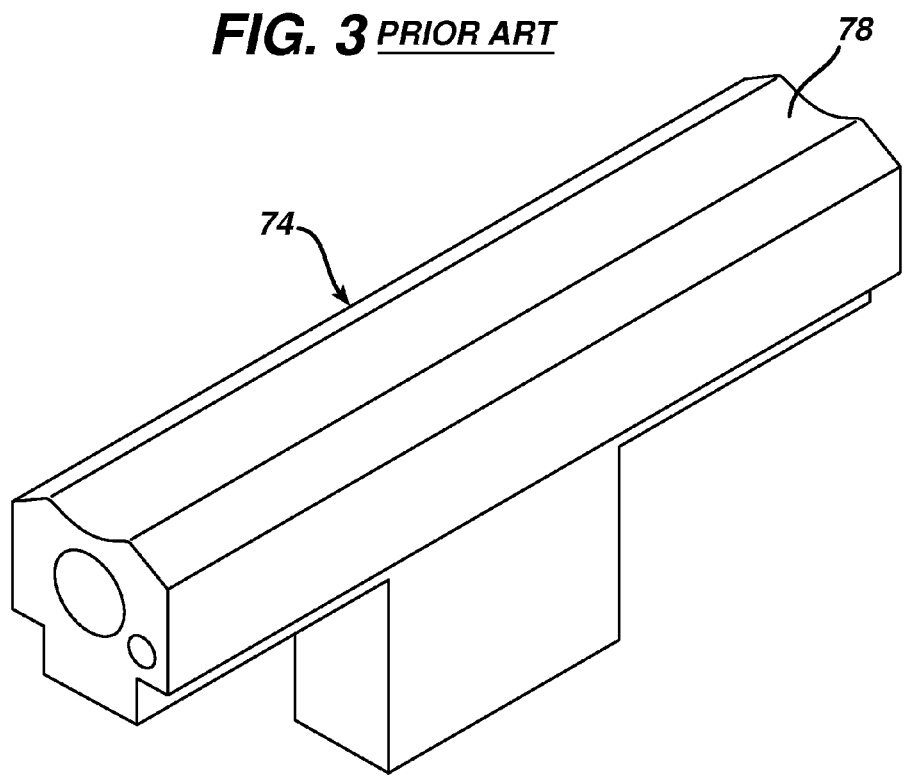
FIG. 3 is a perspective view of a seal bar used to form the tube of FIG. 2.

In an example of prior art (shown FIG. 2), a tube is used to form a wrapper that includes a seam made up of an attachment zone. The attachment zone connecting the layers of material was generally a single, continuous line 76. FIG. 2 shows a tube having this type of seam (the tube capable of being further formed into an overwrap for a tampon). To form such a seam, a sealing bar 74 such as that shown in FIG. 3 is known to be used. This sealing bar has a single sealing surface 78 which forms a single, continuous seal in the overwrap material when it contacts the material. Sealing surface 78 generally conforms to the cylindrical form of a digital tampon. The sealing area made by such a sealing bar can be any width, forming a wide seam that is difficult to tear across.

Figure 4:
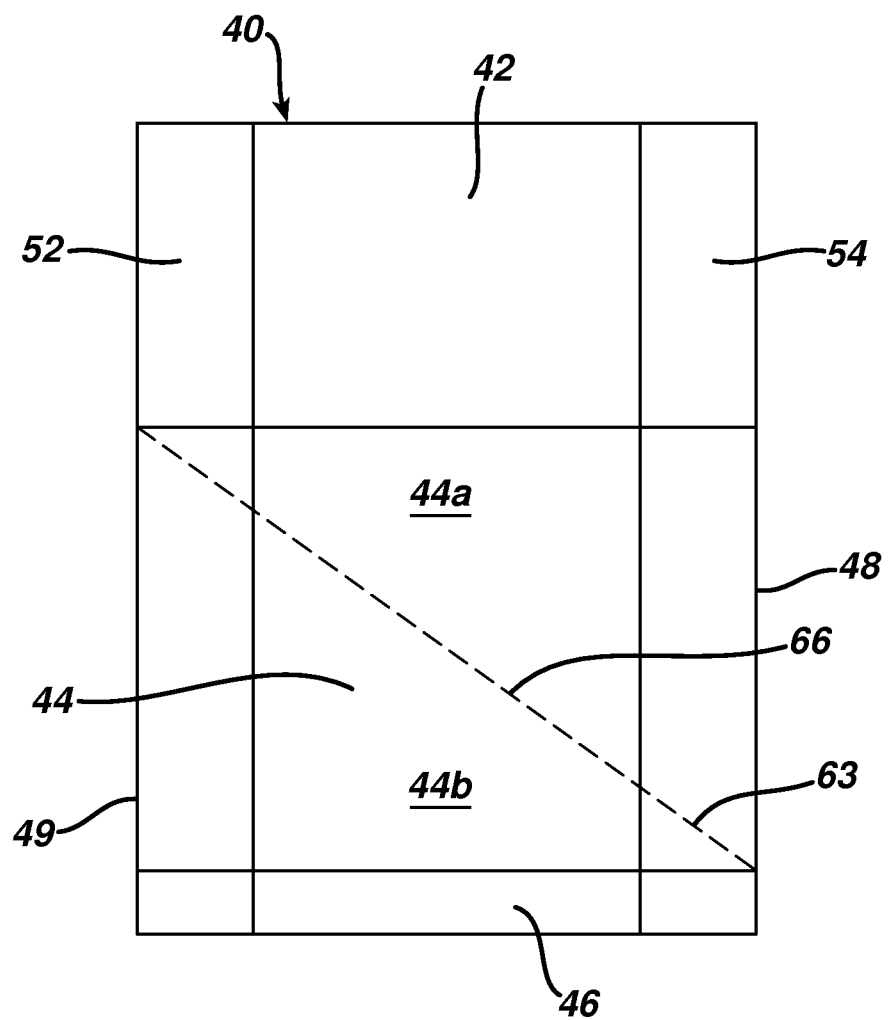
FIG. 4 is a plan view of a material sheet for forming one embodiment of the present invention.

Turning to FIG. 4, there is shown a sheet of overwrap, an example of which is used to form one embodiment of the present invention.

As shown in this figure, the wrapper may be formed from a rectangular sheet of material 40 having an insertion end 42, a withdrawal end 46, a central portion 44, a first margin 52, a second margin 54, a first edge 48, and a second edge 49. The central portion 44 further has upper central area 44a, which is toward the insertion end and lower central area 44b, which is toward the withdrawal end. When sheet 40 is formed into a tubular structure, margins 52 and 54 overlap. These margins may be joined together longitudinally (resulting in a seam down the side of the tampon). The sealing of the margins form a two-layer seam. Ultimately, the tubular structure is closed at both ends to contain the tampon. This results in a package in which the lower portion of the package is formed of the lower central area 44b of the sheet of wrapper material, and the central portion of the package is formed of the upper central area 44a of the sheet.

Figure 5:
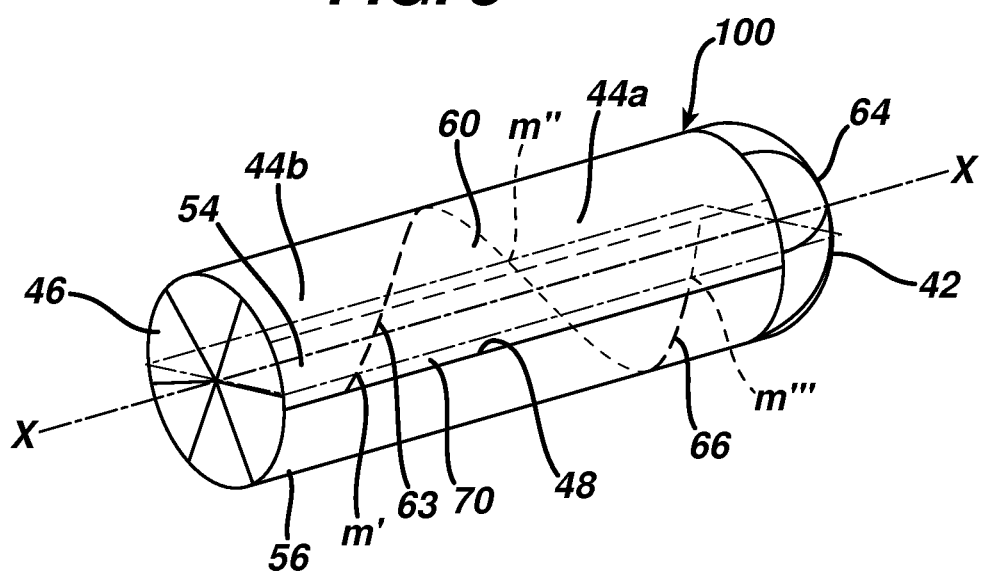
FIG. 5 is a perspective view of a packaged tampon made from the material sheet of FIG. 4.

In this embodiment, there is a single line of weakness 60 made of weakness components 66 and 63. In the embodiment shown in FIG. 4, weakness component 66 is shown as inclining or at a diagonal direction. A tampon contained with the resultant overwrap is shown in FIG. 5.

Additionally by using a specific ratio of weakness:land lengths in specific areas of the overwrap, it is possible to provide an overwrap that opens completely around the tampon, remains in a single unitary piece but provides for hygienic removal of the tampon from the overwrap. For example, using a slit or perforation having an open length as the weakness point, it has been found that a ratio in the range, for example, of approximately 1:1—e.g., about 2:3 to about 3:2, preferably about 4:5 to about 5:4—open length to land length in lower central area 44b (including weakness component 63) and a ratio, for example, of open length to land length in upper central area 44a of approximately 2:1 or greater allows for the user to grasp the insertion end and the withdrawal end with fingers from both hands, twist and/or pull on the overwrap and open the upper central area 44a with a small amount of force. The user would then continue to slightly twist the overwrap to further split the line of weakness 60 into the lower central area 44b. The user can then pull to remove the overwrap from the base with one hand while holding the insertion end. The overwrap on the insertion end remains intact without the user's fingers contacting the tampon. The overwrap remains as a single piece of material. Since the perforations in the upper central area 44a has a greater open length as compared to the open length of the lower central area 44b, the line of weakness 60 will open first in the upper central area 44a before opening in the lower central area 44b. The insertion end of the tampon would remain in the overwrap until the user completely removed the overwrap (just prior to insertion into the body). Of course, the steps of twisting open and pulling off the overwrap can be accomplished in one step. While the above details an example of a ratio for one type of material, the choice of material and basis weight can alter the ratio of open area to land region. The above provides examples of open lengths, land lengths and the ratios between them. These can be balanced so the formed line of weakness 60 is stronger at withdrawal end and weaker in center portion of the packaged tampon. Any ratio that obtains this for a particular material and a particular sized tampon is acceptable, however, the line of weakness should be optimized to permit the overwrap to withstand 1) internal expansion forces from the tampon as the compressed fibers tend to relax over time and 2) external forces from the environment (such as those exerted on the overwrap when a consumer stores the tampon in a purse or pants pocket) without rupturing the line of weakness.

Weakness components 66 that are located primarily in the upper central area 44a have an open length to land length ratio of approximately 2:1. In one embodiment, the open length to land length in the upper central area 44a is 900:400 (μm) and the open length to land length in the lower central area 44b is 450:550 to 500:500 (μm).

The line of weakness does not necessarily have to be straight. As formed in the overwrap, the weakness components and resultant line of weakness may be a diagonal line, a curved line or a line that changes direction by e.g. having angles, curves, and/or inflections such as inflection points. In order to obtain the line of weakness in this type of embodiment, the sheet of material will need to have the weakness components in the appropriate pattern. In one embodiment, the line of weakness originates in the withdrawal portion of the tampon and inclines such that it terminates in the central portion. Again, the line of weakness can be inclined at an angle from the plane perpendicular to the longitudinal axis. The angle of inclination is balanced against the desire to maintain the wrapper in a single piece. The smaller the angle, the greater the component of force applied to the package is translated into shear force that is able to rupture the line of weakness. However, a small angle of inclination provides greater opportunity for the wrapper material to tear between the ends of the line of weakness to result in two separated package remnants. The larger the angle, the lesser opportunity for the wrapper material to tear between the ends of the line of weakness to result in two separated package remnants.

In another embodiment, the line of weakness originates in the lower 5-25% of the sheet and terminates in the insertion portion. In still another embodiment, the line of weakness is not a straight line but a curved line that originates in the withdrawal portion of the tampon, extends into the central portion and terminates in the withdrawal portion. In these embodiments, the withdrawal end portion of the overwrap is easily removed after the line of weakness has been ruptured, which leaves the insertion portion of the overwrap somewhat intact. This allows the user to further handle the tampon without actually contacting or contaminating the insertion end of the tampon.

In a preferred embodiment, the line of weakness according to the present invention extends completely around the perimeter of the tampon. As used herein, the term "extends completely around the perimeter" shall mean that the line of weakness is continuous 360° about the circumference of the outer surface 20 of the intravaginal device.

When placed on a tampon, the overwrap has a continuous line of weakness which includes the two-layer seam. The line of weakness therefore extends completely around the perimeter of the encased tampon. When used to wrap the tampon, the overwrap has a line of weakness 60 that may have one end near the withdrawal end 18 of the tampon and another end disposed toward the insertion end 14. In one embodiment, the line of weakness is arranged and configured such that when the resulting overwrap is opened, the portion holding the insertion end of the tampon remains on the tampon and the portion holding the withdrawal end of the tampon also remains on the tampon but can be easily pulled off.

The overlapping of the margins and sealing does not compromise the line of weakness such that when the user opens the overwrap, the line of weakness tears completely around and through the sealed overwrap. The seal does not prevent the line of weakness from extending through overlap region to effectively propagate a tear through this overlap region. If the line of weakness is formed from a series of slits, the forming of the seam in the margins will not close up the slits; rather the slits remain open sufficiently to be easily ruptured.

Upon the rupturing of the line of weakness, the resultant open overwrap can be removed as a unitary piece of material. As the line of weakness originates and ends at different parts of the seam, the line of weakness will not cause division of the wrapper into separate pieces upon opening. The end and origin of the line of weakness are sufficiently separated so as not to overlap and to reduce the likelihood of an undesired tear continuing between them.

The seam not only connects the layers of material together but provides a barrier which prevents contaminants from penetrating into the packaged article. The seam may be any thickness depending on the materials being joined together and the outer conditions. For example, a seal that is expected to provide water protection may be thicker than a seal used to prevent air penetration (for example, the seal used to wrap dry foodstuffs). In this invention, the thickness of the seal or seam is not critical.

Seam 70 may have any dimension that securely holds the overlaid margins together. While it is preferred that the edge 48 of the margin forming the outer surface is securely sealed against the lower material, it is not necessary for the seam to extend to the edge.

As previously stated, when sheet 40 is formed into a tube for holding a tampon, margins 52 and 54 overlap and are joined to form a two layer seam 70. In one embodiment, sheet 40 is a single ply of material such that when margins 52 and 54 are overlapped, the two layer seam has two plies. As the embodiment of FIG. 5 shows a single line of weakness, the resulting wrapped material will have a single ply of weakened material. However, another embodiment may incorporate additional short segments of weakening elements that may be registered to each other and overlap to form one continuous line of weakness 60 with the weakened plies aligned. See, for example, FIG. 11, which is discussed later.

In the embodiment shown in FIG. 5, the second margin overlays the first margin and partially forms the outer surface of overwrap 100. The overwrap is substantially a tube-like cylinder. Both ends are closed such that the tampon within the overwrap is completely contained within the overwrap and separated from the environment. Seam 70 extends to edge 56 of margin 54 and forms a relatively smooth surface. The intravaginal device in this figure has longitudinal axis XX, which extends through insertion end 42 to withdrawal end 46. Shown in FIG. 5 is a plane extending outward from and including longitudinal axis XX. The line of weakness intersects this plane at at least three unique locations, as the line of weakness extends 360° around the perimeter of the tampon. The unique locations include where the plane intersects the two weakness components in the wrapper margins and the weakness component located between the margins. Thus, the plane intersects the line of weakness at at least three unique locations—m', m", m'''.

The longitudinal seam is a longitudinal attachment zone, which connects the overlapping margins (52 and 54) together. In this invention, the longitudinal attachment zone is not a single, continuous seal line but rather may be multiple seals lines which are discontinuous and off-set to each other. This will be further explained below.

Figure 6:
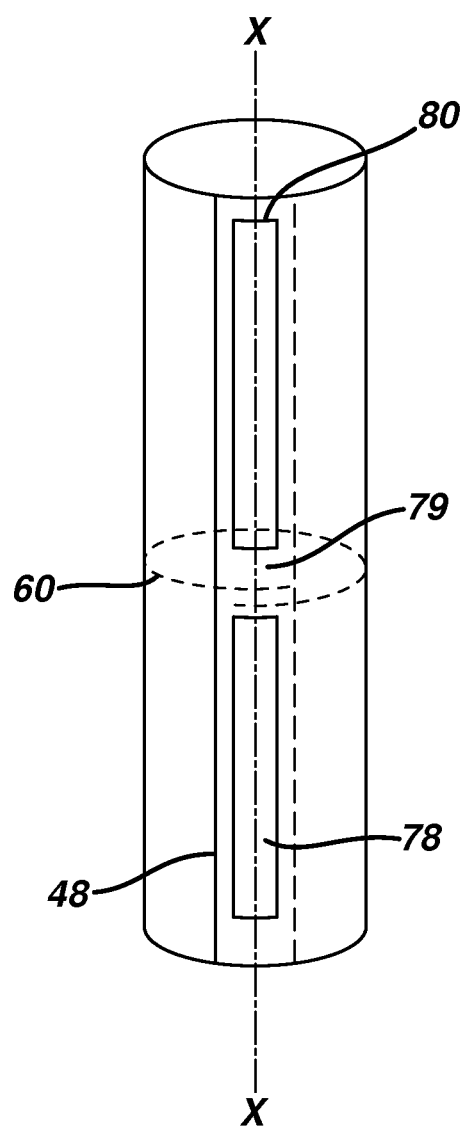
FIG. 6 is a perspective view of a tube having a sealing pattern made according to one embodiment of the invention.

In one embodiment of the invention (shown FIG. 6), the seam 80 is made of at least one attachment zone 78. Attachment zone 78 has a gap 79 through which the line of weakness 60 extends. This allows the line of weakness to extend around 360° the perimeter.

Figure 7:
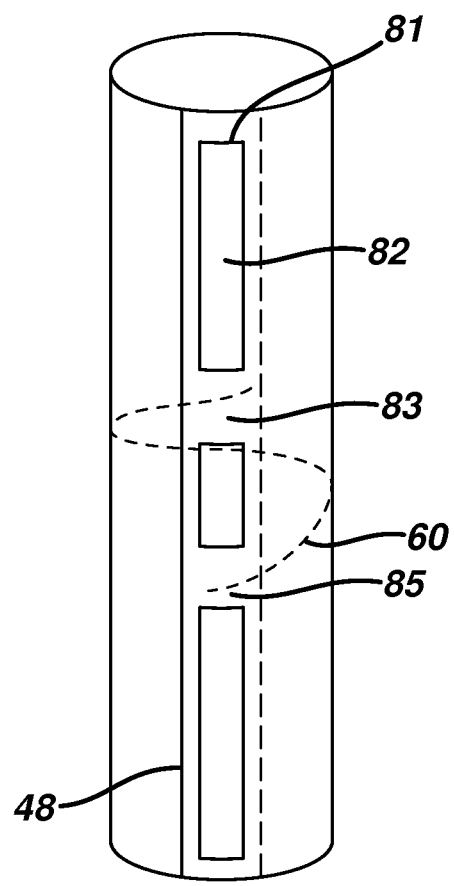
FIG. 7 is a perspective view of a tube having a sealing pattern made according to another embodiment of the present invention.

Another embodiment is shown in FIG. 7. Seam 81 has first attachment zone 82 which has two gaps, 83 and 85. The attachment zone is substantially longitudinal and defines the sides of the seam. The line of weakness extends through the gaps when the seam is sealed and is therefore not affected by any sealing mechanisms such as a sealing bar.

Figure 8:
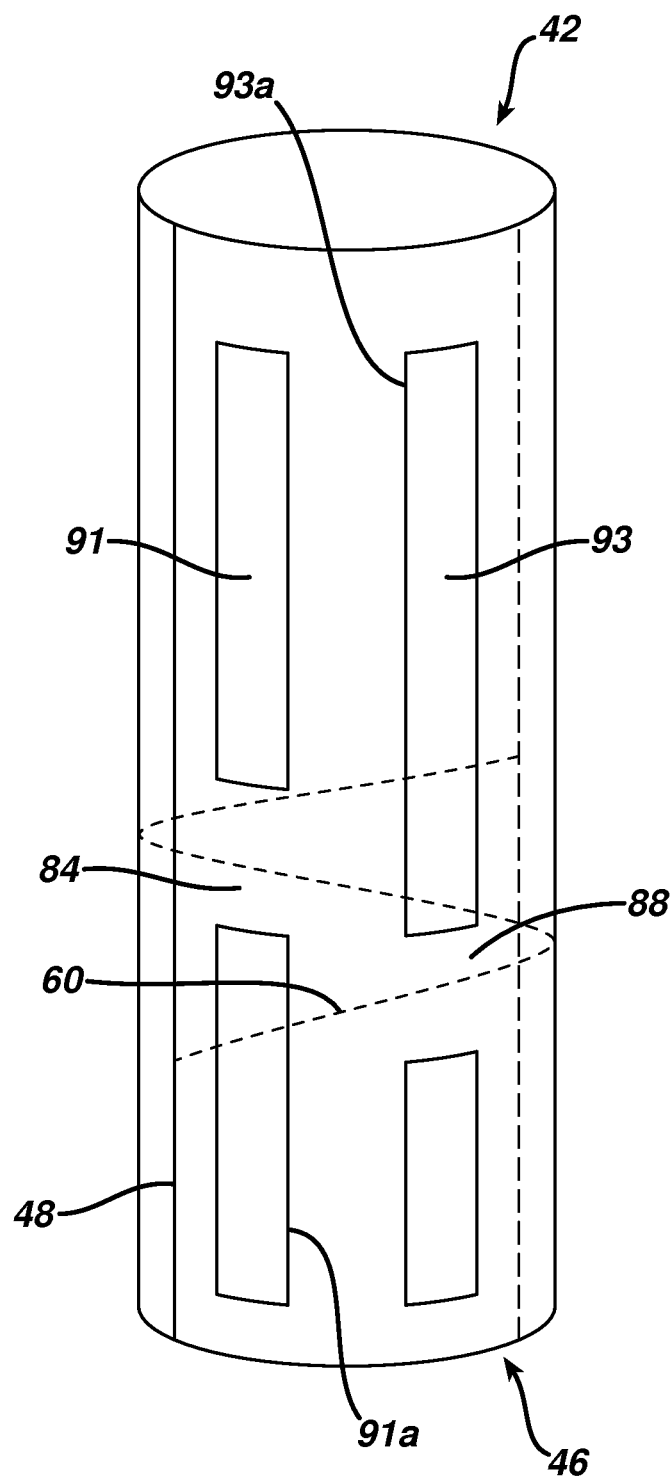
FIG. 8 is a perspective view of a tube having a sealing pattern made according to the present invention.

A third embodiment of the sealing pattern is shown in FIG. 8. In this embodiment, attachment zones 91 and 93 have gaps 84 and 88, respectively, which are off set to each other or at different distances from the end of the overwrap. Attachment zone 91 is opposite attachment zone 93. If the line of weakness has a first end disposed in the seam area at a distance from the end of the overwrap (one of the embodiments) and has a second end disposed at a second distance from the end of the overwrap, then the first and second gaps must be located such that the line of weakness falls within the two areas not sealed or covered by the gaps. As previously mentioned, while in this embodiment the gaps are such that there is a staggered unsealed spaces, it is possible that the gaps would be aligned perpendicularly to the longitudinal axis of the tampon when completed tampon is completely sealed by the overwrap. What is critical is that the unsealed portion spans the width of the seam such that the line of weakness substantially goes around the perimeter of the tampon. In looking at FIG. 8, a line of weakness might begin at either of the edges of attachment zone 91, extend through gap 88, continue around the outer surface of the overwrap, go through gap 84 and end at either of the edges of attachment zone 93. In the figure, edges 91a and 93a are shown to illustrate one possible embodiment. The edges of the attachment extend to and include the edges of the gaps. In this embodiment, line of weakness 60 begins at edge 91a, extends through gap 88 in attachment zone 93, extends around the product and through gap 84 in attachment zone 91, and ends at edge 93a. While some elements of the line of weakness 60 extend between edge 48 of the overwrap material and edge 91a of the attachment zone 91, these may or may not be effective as a line of weakness as the attachment zone 91 may compromise the ability of the line of weakness 60 to actually significantly weaken the overwrap material at that area. Nonetheless, the line of weakness 60 still can extend around more than 360° of the package in this embodiment.

In another embodiment of the present invention (shown FIG. 9), the seam 100 has three attachment zones. While seam shown runs generally in the longitudinal direction, other directions are possible. Attachment zones 120, and 160 have gaps 130, 170, respectively. Attachment zone 140 in this figure has two gaps, 150 and 155 although it is possible to have a single gap that is longer in the longitudinal direction and essentially has an unsealed area that encompasses gaps 150 and 155. While the width of each attachment zone is not of particular importance, the seam must be robust. One way to provide robustness is to ensure that the overall surface of the sealing bar has a similar configuration to match the object being sealed. This adds to the robustness of the seal during packaging and handling of the finished product.

Figure 9:
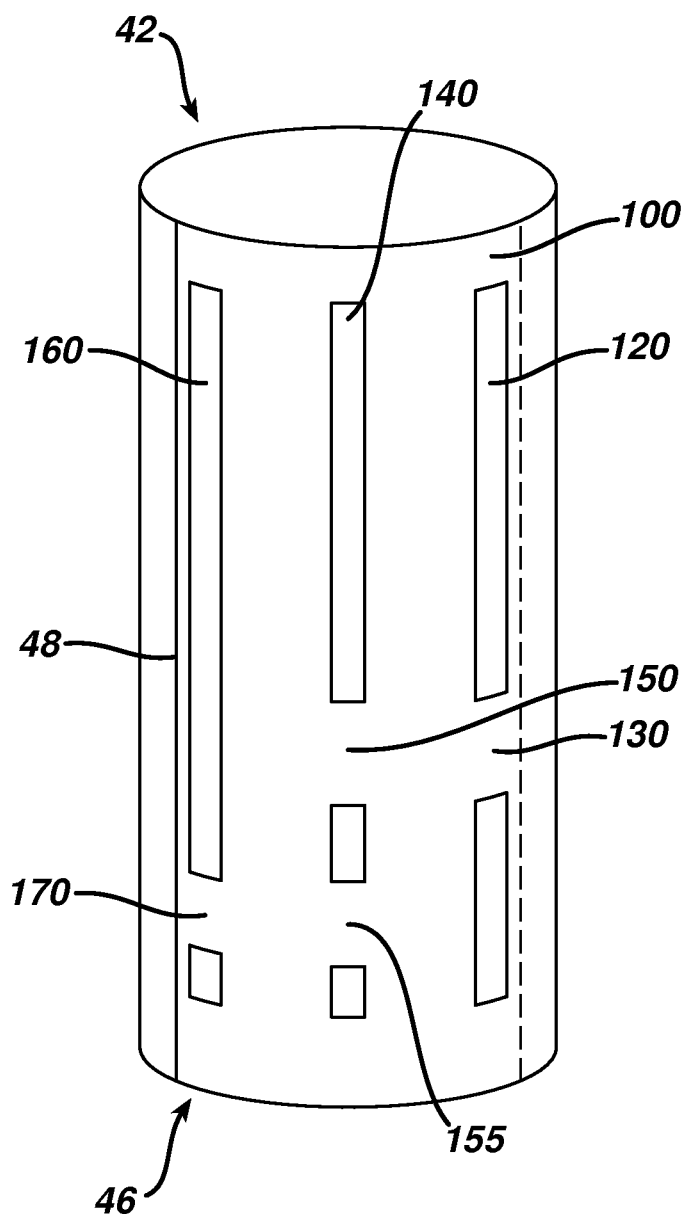
FIG. 9 is a perspective view of a tube having another sealing pattern made according to the present invention and made from the material sheet of FIG. 4.
Figure 10:
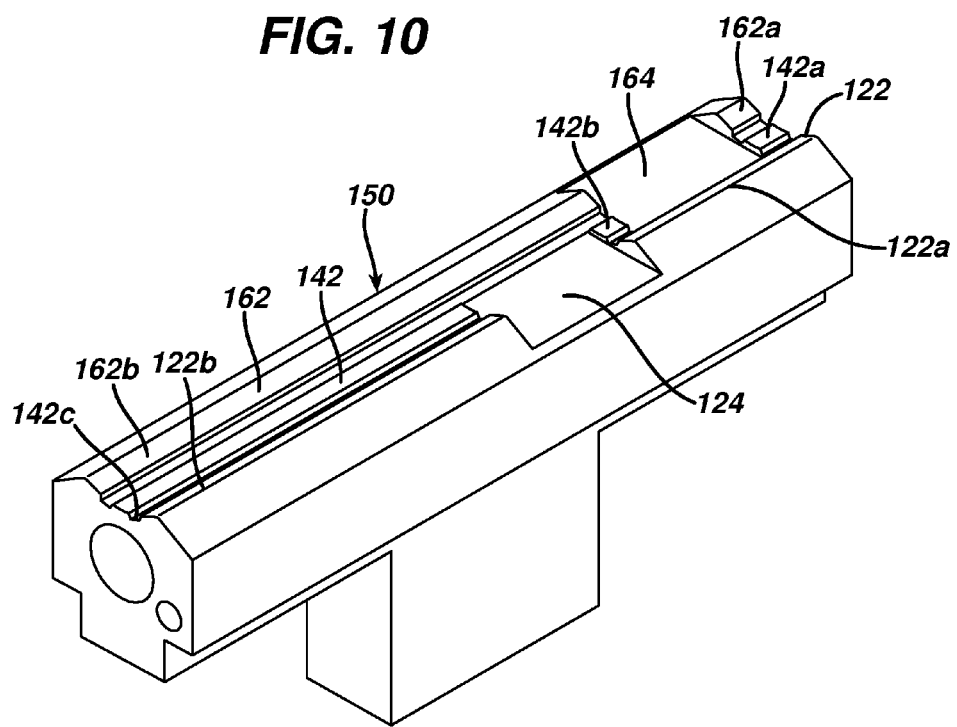
FIG. 10 is a perspective view of a seal bar used to form the tube of FIG. 9.

The sealing bar used to form the sealing pattern of FIG. 9 is shown in FIG. 10. As shown, the sealing bar 150 has three sealing surfaces 122, 142 and 162, which form attachment zones 120, 140 and 160 (shown FIG. 9), respectively. Each sealing surface has at least two portions. For sealing surface 122, there is upper sealing surface 122b and lower sealing surface 122a. Lower sealing surface 122a seals that portion of the sheet that contacts the string end of the tampon and upper sealing surface 122b seals the portion corresponding to the insertion portion of the tampon. For sealing surface 142, there is upper sealing surface 142c, mid sealing surface 142b and lower sealing surface 142a. As previously stated, mid sealing surface 142b may be eliminated. For sealing surface 162, there is upper sealing surface 162b and lower sealing surface 162a. Sealing surface 122 has a sealing gap 124, which lies between the upper and lower portions and corresponds to attachment gap 130. Sealing surface 162 has a sealing gap 164, which lies between the upper and lower portions and corresponds to attachment gap 170. As shown, attachment gaps 155 and 170 are located at a similar distance from the withdrawal end of the wrapper. Similarly, attachment gaps 150 and 130 are also at similar distances from the withdrawal end.

Figure 11:
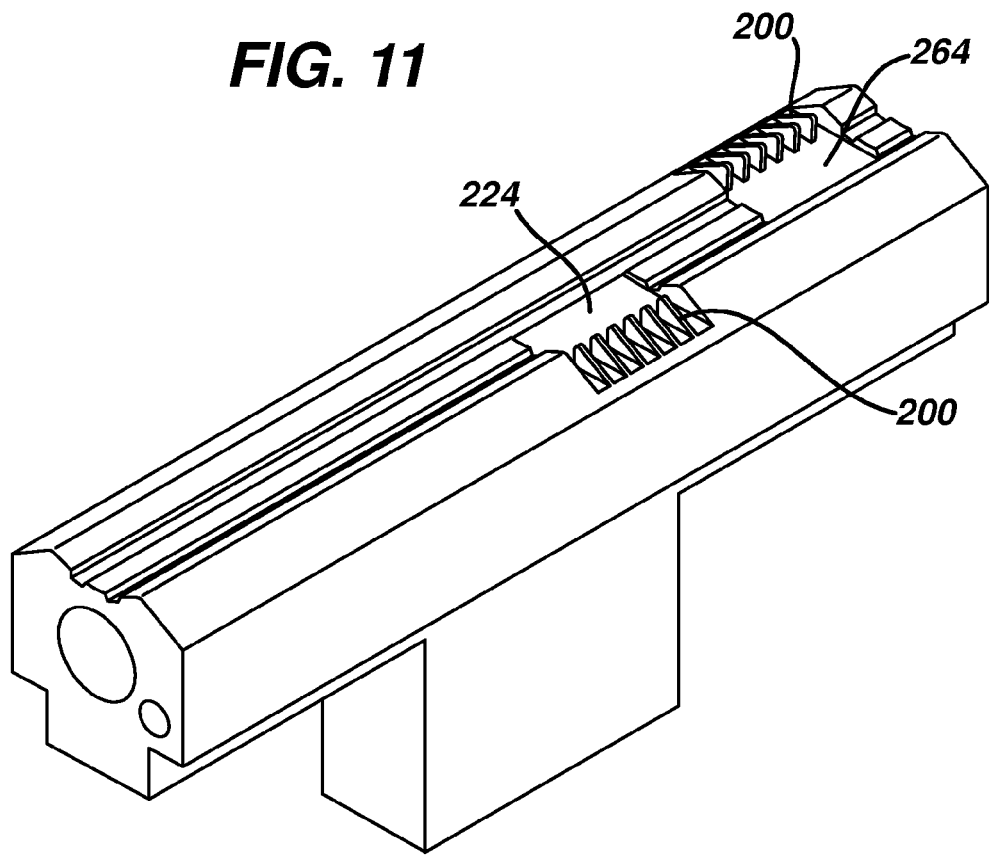
FIG. 11 is a perspective view of a seal bar useful in an alternate embodiment of the present invention.
Figure 12:
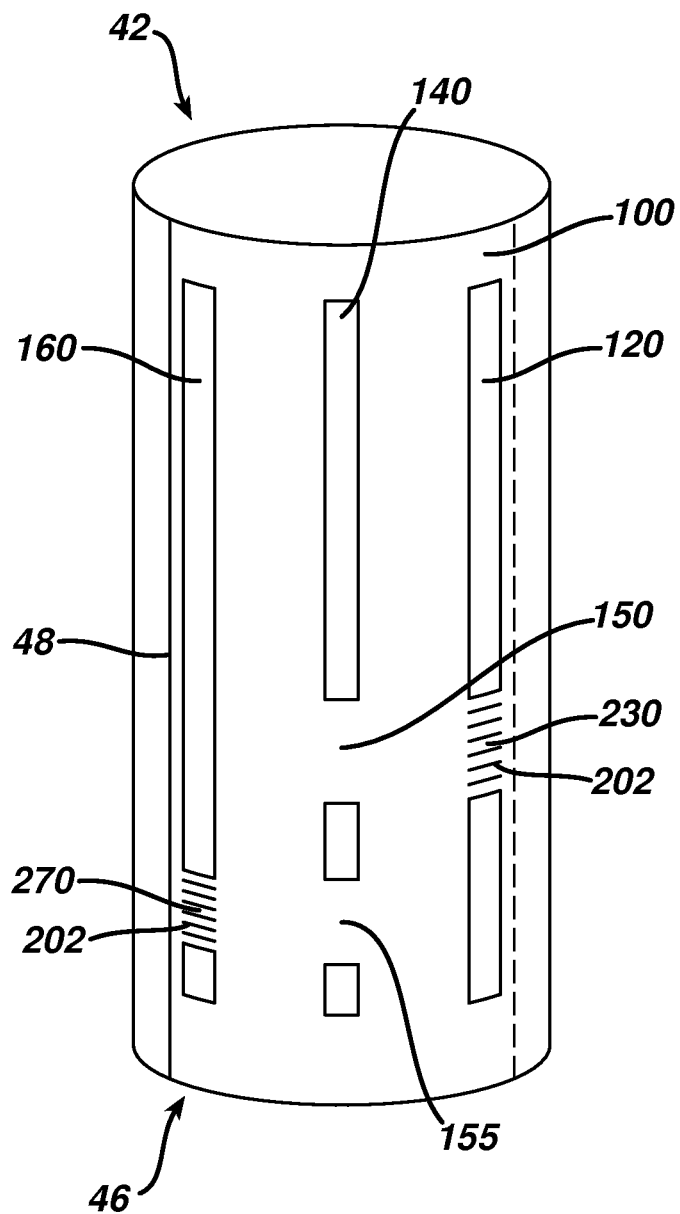
FIG. 12 is a perspective view of a tube formed with the sealing bar of FIG. 11.

In another embodiment of the sealing bar shown in FIG. 11, the sealing gaps 224 and 264 may include discrete raised portions 200 that result in small, discrete attachments 202 within the larger attachment gaps 230 and 270 as shown in FIG. 12. The small, discrete attachment may be in the form of dots, dashes, or any other geometric pattern.

Figure 13:
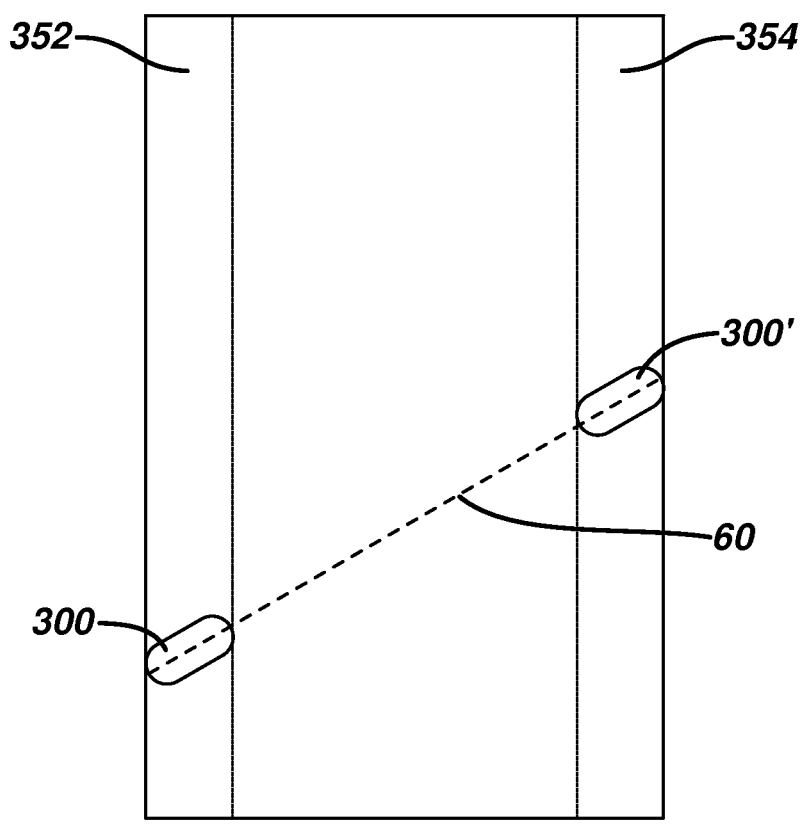
FIG. 13 is a plan view of a material sheet for forming an alternate embodiment of the present invention having coated, un-sealable regions.

Another way to obtain sealing gaps (e.g. gap 79 in FIG. 6; gaps 83 and 85 in FIG. 7; gaps 84 and 88 in FIG. 8; and gaps 130, 150, 155 and 170 in FIG. 9) is to use a solid sealing element such as that in the prior art (FIG. 3) on a wrapper material that is partially coated with a material that is not thermally bondable. For example, using a lacquer to coat specific areas within the overlap and then exposing the overlap to a continuous sealing bar would result in a seam having an attachment zone containing gap areas. Any material that is not thermally bondable may be used to prevent the seam from forming continuously. The material may be coated, for example, on the appropriate sides of overlapping margins. An example of a line of weakness 60 which has coatings 300, 300' is shown in FIG. 13. These coated areas do not bond when margins 352, 354 over lap to form the seam.

Figure 14:
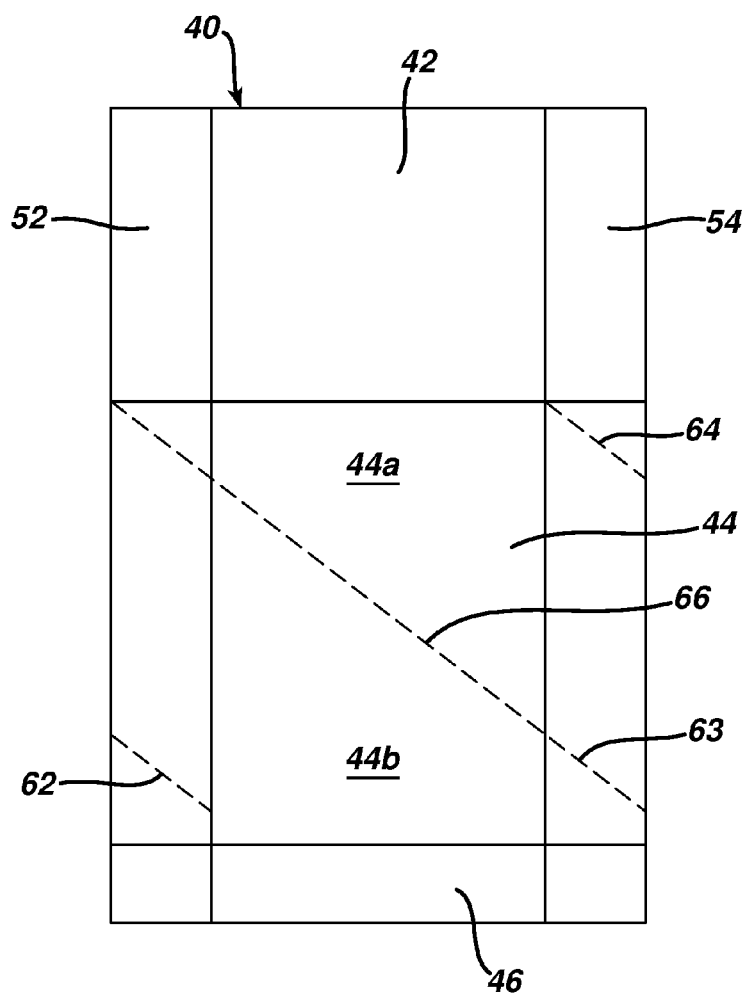
FIG. 14 is a plan view of a material sheet for forming an alternate embodiment of the present invention.

FIG. 14 illustrates an alternate material sheet having a line of weakness that could be formed into an overwrap using a sealing pattern shown in FIG. 9. The sealing pattern formed by the sealing bar of FIG. 10 would allow the line of weakness to extend into the seam without having the perforations compromised. In contrast to the embodiment of FIG. 5 this material incorporates additional short segments (62, 64) of weakening elements that may be registered to other elements of the line of weakness and overlap to form one continuous line of weakness 60 with the weakened plies aligned.

In other embodiments, the sealing pattern may be variations of the previously described. The lengths of the attachment zones and placement of attachment gaps may be varied in order to accommodate multiple lines of weaknesses or a line of weakness with a steep incline. For example, a middle attachment zone (such as attachment zone 140 shown in FIG. 9) may be such that gap 150 is closer to the insertion end than the withdrawal end. Likewise, gap 130 would be located at a similar distance such as gap 150. This staggering or offsetting of the gaps allows a line of weakness to extend into the gaps without becoming part of the sealed attachment zone. The distance or placement of the gaps can be optimized based on the line of weakness angle, material used or thickness of the tampon being packaged.

The opening of the wrapper that has a sealing pattern (FIGS. 7, 8, and 9) described for releasing the tampon along the line of weakness (such as shown in FIG. 5) results in an initial tearing step, during which the overwrap 100 mainly tears at an angle, diagonally or at an incline around the perimeter of the tampon 10 and a subsequent step, during which the tampon is removed from the opened overwrap 100. The angle-like or diagonal opening of the overwrap results in a large open area, which allows for the tampon to be easily removed with little manipulation. The opened overwrap remains in a unitary piece, which provides for easy removal and disposal with one hand. The problem of having multiple small pieces of wrapper clinging to the user's fingers or falling into a toilet is thereby eliminated.

It is generally preferred according to the present invention that the distance between adjacent weakness points is substantially equal throughout the line of weakness. However, if desired, varied spacing can be employed to affect the tearing force profile (increase/decrease of tearing force upon tear propagation) experienced by the user as she opens the wrapper along the line of weakness. A particularly preferred embodiment of the line of weakness of the present invention is a line of weakness extending completely around a part of the perimeter of the wrapped tampon, and in some embodiments, the line of weakness extends around more than the perimeter of the wrapped tampon.

The absorbent materials useful in the formation of the absorbent body include fiber, foam, superabsorbent, hydrogels and the like. Preferred absorbent material for the present invention includes foam and fiber. Absorbent foams may include hydrophilic foams, foams which are readily wetted by aqueous fluids as well as foams in which the cell walls that form the foam themselves absorb fluid.

Preferably, the fibers employed in the formation of the absorbent body include regenerated cellulosic fiber, natural fibers and synthetic fibers. Preferably, the materials employed in the formation of a tampon according to the present invention include fiber, foam, hydrogels, wood pulp, superabsorbents, and the like. A useful, non-limiting list of useful absorbent body fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body.

The tampon blank may be substantially surrounded or enclosed by a fluid-permeable cover. Thus, the cover encloses a majority of the outer surface of the tampon. This may be achieved as disclosed in Friese, U.S. Pat. No. 4,816,100, or Lochte; et al., US Pub. App. No. US 2008/0064581 A1, entitled "Tampon Having Apertured Film Cover Thermobonded to Fibrous Absorbent Structure", the disclosures of which are herein incorporated by reference. In addition, the insertion end 14 of the tampon or the opposite withdrawal end 18, or both may be enclosed by the cover. Of course, for processing or other reasons, some portions of the surface of the tampon 10 may be free of the cover. For example, the insertion end 14 of the tampon 10 and a portion of the cylindrical surface adjacent this end may be exposed, without the cover to allow the tampon 10 to more readily accept fluids.

The cover may be a nonwoven or apertured polymeric film. The cover can ease the insertion of the tampon 10 into the body cavity and can reduce the possibility of fibers being separated from the tampon 10. Apertured polymeric films useful in forming the cover are known to those of ordinary skill in the art.

Examples for wrapper materials suitable for use with the present invention are polymeric films made of polyethylene, polypropylene, polyester, cellophane, polyamide, poly(vinyl chloride), ethylene-vinyl acetate copolymer and the like. Alternatively, heat-shrinkable films, stretch films, prestretched elastic films and biodegradable material can be used to form the wrapper of the present invention. While not limited to a given composition, preferred compositions of heat-shrinkable and stretch films comprise primarily polyolefins such as polyethylene and polypropylene, or poly(vinyl chloride). Polystyrene and polyethylene-terephtalate (PET), although being not heat sealable, are also suitable for use with the present invention. In one embodiment of the present invention, the wrapper material is formed from a coextruded polypropylene film. Wrappers consisting of those materials can be closed by gluing with an adhesive. Other generally occlusive materials include metallic foils, such as aluminium foil. While occlusive wrapper materials are often preferred, in other situations non-occlusive or porous materials can be used, such as nonwovens, wovens, scrims, meshes and papers. Such non-occlusive materials can be made occlusive by combinations such as by lamination with or by coating with occlusive material. In the case of cellulosic papers, examples include lamination with a polymeric film such as a polyolefinic composition or coating or impregnation of the paper with wax. The aforementioned materials can be coated with various chemical compounds to improve their barrier properties or the ability for sealing. Any suitable combination of the aforementioned materials is also within the scope of the present invention. In some embodiments, the materials suitable for use as wrapper materials with the present invention are heat-sealable for forming the wrapper by closing the wrapper material via heat-sealing onto itself after having wrapped the tampon. Thereby a seam is generated in the regions of the wrapper, which were exposed to heat. Alternatives for closing the wrapper material are gluing, embossing, crimping, sewing, stitching, entangling, mechanical interlocking, cold pressure welding, or ultrasonic bonding. The seam may be a series of discrete elements or may be a continuous seal. In some embodiments, the wrapper materials for use herein have a low flexural modulus for providing a low noise tampon wrapper during transport as well as during handling, i.e. opening of the wrapper.

Also included in this invention is a method of packaging a tampon, which includes the steps of providing a wrapper blank comprising a flexible, sheet-like material having a width and a length and at least one line of weakness extending across substantially all of the width; forming the wrapper blank into a wrapper tube having first and second ends, a length corresponding to the length of the wrapper blank, and an overlapping longitudinal seam area having two plies of the flexible, sheet-like material; forming a longitudinal seam within the seam area by attaching portions of the two plies together in a pattern. The seam has a first, substantially longitudinal attachment zone that defines a first side of the seam area and a second substantially longitudinal attachment zone, opposite the first substantially longitudinal attachment zone that defines a second side of the seam area. The second substantially longitudinal attachment zone has a gap formed therein proximate a first end thereof corresponding to the first end of the wrapper tube. The first substantially longitudinal attachment zone has a gap formed therein proximate a first end thereof corresponding to the first end of the wrapper tube.

The gap in the second substantially longitudinal attachment zone is nearer the first end of the wrapper tube than the gap in the first substantially longitudinal attachment zone. The line of weakness has a first end disposed within the seam area adjacent the first substantially longitudinal attachment zone, which extends through the gaps in the second and first substantially longitudinal attachment zones and a second end disposed within the seam area adjacent the second substantially longitudinal attachment zone. The first end of the tube is then closed; the tampon inserted into the tube and the second end of the tube is closed.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A packaged tampon comprising a substantially cylindrical wrapper formed of a flexible, sheet-like material that contains the tampon, wherein:
    a. the substantially cylindrical wrapper is closed at both ends and has a longitudinal seam area in which overlapping portions of the flexible, sheet-like material are attached to each other to form a tubular structure;
    b. the longitudinal seam area comprises a substantially longitudinal attachment zone with a first edge and a second edge that together define a seam area; and wherein:
    c. a line of weakness:
        i. has a first end disposed within the seam area at the first edge of the substantially longitudinal attachment zone and disposed at a first distance from a first end of the tubular structure;
        ii. extends through a gap in the substantially longitudinal attachment zone and to the second edge of the substantially longitudinal attachment zone;
        iii. continues generally circumferentially about the wrapper; extends through the gap in the substantially longitudinal attachment zone; and
        iv. terminates at a second end disposed within the seam area at the second edge of the substantially longitudinal attachment zone, the second end disposed at a second distance from the first end, wherein the second distance from the first end is different than the first distance from the first end.

2. The packaged tampon of claim 1, wherein the packaged tampon has a lower portion disposed at a withdrawal end of the tampon and a central portion disposed between the withdrawal end and an insertion end of the tampon.

3. The packaged tampon of claim 2, wherein the line of weakness is formed of perforations having open portions and land portions, each having a length.

4. The packaged tampon of claim 3, wherein the ratio of open portion length to land portion length is greater in the central portion of the packaged tampon than in the lower portion.

5. The packaged tampon of claim 4, wherein the ratio of open portion length to land portion length is about 2:1 in the central portion of the packaged tampon.

6. The packaged tampon of claim 4, wherein the ratio of open portion length to land portion length is between 2:3 and about 3:2 in the lower portion of the packaged tampon.

7. The packaged tampon of claim 1, wherein the line of weakness is inclined at an angle from a plane perpendicular to the longitudinal axis of the packaged tampon.

8. The packaged tampon of claim 1, wherein at least one gap in the substantially longitudinal attachment zone has discrete attachments disposed within the gap.

* * * * *